United States Patent [19]

Arroyo

[11] Patent Number: 5,276,070

[45] Date of Patent: Jan. 4, 1994

[54] BONE CEMENT

[75] Inventor: Nestor A. Arroyo, East Windsor, N.J.

[73] Assignee: Pfizer Hospital Products Group, Inc., New York, N.Y.

[21] Appl. No.: 860,260

[22] Filed: Mar. 31, 1992

Related U.S. Application Data

[63] Continuation of Ser. No. 471,193, Jan. 25, 1990, abandoned.

[51] Int. Cl.5 ............... A61L 25/00; C09J 133/12; C08F 265/06
[52] U.S. Cl. .................... 523/117; 523/116; 525/309; 526/329.2
[58] Field of Search .............. 523/116, 117; 525/309; 526/329.2

[56] References Cited

U.S. PATENT DOCUMENTS

| | | | |
|---|---|---|---|
| 4,159,288 | 6/1979 | Carson | 525/228 |
| 4,268,639 | 5/1981 | Harturst et al. | 525/303 |
| 4,341,691 | 7/1982 | Anuta | 523/116 |
| 4,490,497 | 12/1984 | Evrard | 525/309 |
| 4,500,658 | 2/1985 | Fox | 523/117 |
| 4,554,686 | 11/1985 | Charles Baker | 623/16 |
| 4,837,279 | 6/1989 | Arroyo | 525/193 |
| 4,910,259 | 3/1990 | Kindt-Larsen | 523/117 |

FOREIGN PATENT DOCUMENTS

| | | |
|---|---|---|
| 0080405 | 6/1983 | European Pat. Off. |
| 0218471 | 4/1987 | European Pat. Off. |
| 0330346 | 8/1989 | European Pat. Off. |
| WO86/02370 | 4/1986 | PCT Int'l Appl. |
| 1532318 | 11/1978 | United Kingdom |
| 2219303 | 12/1989 | United Kingdom |
| 2069517 | 8/1991 | United Kingdom |

*Primary Examiner*—David J. Buttner
*Attorney, Agent, or Firm*—Peter C. Richardson; Lawrence C. Akers; Raymond W. Augustin

[57] ABSTRACT

There is disclosed a bone cement composition comprising (a) a liquid component comprising a monomer of an acrylic ester and (b) a powdered component comprising a terpolymer of methyl methacrylate, butyl methacrylate, and styrene. A prepared terpolymer, based on the weight of the powdered component, has between 55 to 89.5% methyl methacrylate, 10 to 40% butyl methacrylate and 0.5 to 5% styrene.

8 Claims, 1 Drawing Sheet

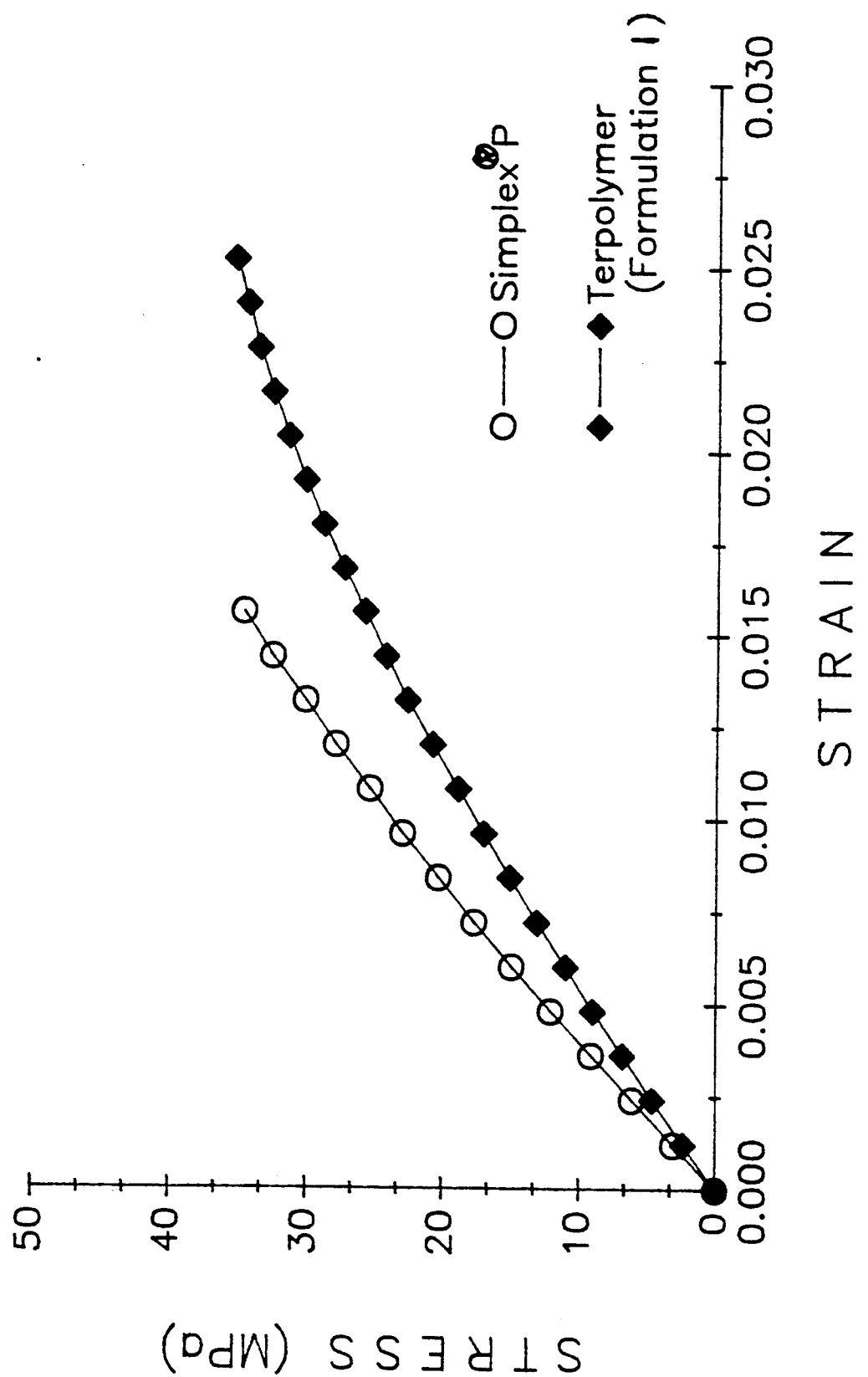

BONE CEMENT

This a continuation of application Ser. No. 471,193, filed on Jan. 25, 1990, now abandoned.

BACKGROUND OF THE INVENTION

1. Field of the Invention

The present invention relates to a bone cement composition. More particularly, the present invention relates to a bone cement wherein the liquid component comprises a monomer of an acrylic ester and the powdered component comprises a terpolymer of methyl methacrylate, butyl methacrylate, and styrene.

2. Description of the Prior Art

Bone cements find wide usage in a variety of applications. For instance, they are used for cementing implants in place, for the anchoring of endoprostheses of the joints, in the treatment of skull defects, and for the performance of spinal fusion. These cements are typically polymeric materials and the surgeon usually mixes the interactive components to make the cement at an appropriate stage during the surgical procedure. Typically, the components of the bone cement comprise a powdered homopolymer or copolymer of methyl methacrylate and a suitable liquid monomer, for example, methyl methacrylate. To accelerate the polymerization of the bone cement, a catalyst system may also be used. The catalyst, if present, is in the form of a redox catalyst system, usually containing an organic peroxy compound, such as dibenzoyl peroxide, plus a reducing component, such as p-toluidine Once the bone cement/implant combination, for example, is in the body, the surgeon will later wish to inspect the implant by X-rays and since the polymers and/or monomers are relatively radiolucent, radiopaque materials, also called opacifiers, are added to the polymeric bone cement. Examples of such opacifiers are barium salts, such as barium sulphate, and other salts such as zirconium oxide and zinc oxide. While these opacifying agents give the necessary radiopacity, it has been reported that they tend to reduce the mechanical properties, e.g. transverse strength and compressive strength of the set polymeric bone cement. The reported solution to this alleged problem of reduced mechanical strength is referred to in a number of patents.

U.S. Pat. No. 4,500,658 refers to a method of incorporating an opacifier in an acrylic resin by suspension polymerization.

EPO Patent Application No. 0218471 refers to a composition for forming a bone cement comprising a powdered component and a monomer component, the powdered component comprising ethyl methacrylate polymer beads incorporating particles of opacifier therein and the monomer component comprising n-butyl methacrylate.

U.S. Pat. No. 4,341,691 refers to a low viscosity bone cement comprising a liquid methyl methacrylate monomer and powdered polymethylmethacrylate beads wherein 85-95% of the polymethylmethacrylate beads fall through a #40 mesh and #100 mesh screen and 5-15% of the polymethylmethacrylate beads pass through a #40 mesh screen but not through a #100 mesh screen.

U.S. Pat. No. 4,554,686 refers to a frozen polymethylmethacrylate bone cement.

U.S. Pat. No. 4,268,639 refers to a bone cement prepared by mixing a finely powdered solid polymer phase of polymethylmethacrylate and/or poly (2-hydroxyethyl methacrylate) with a liquid monomer phase of methyl methacrylate and/or 2-hydroxyethyl methacrylate in a weight ratio of polymer phase to monomer phase of 1.5 to 3.3:1.

United Kingdom Patent No. 1,532,318 refers to a bone cement comprising a liquid component comprising methyl methacrylate as an emulsion in water and a powdered component comprising polymethylmethacrylate in finely divided form.

U.S. Pat. No. 4,837,279 refers to a bone cement comprising (a) a liquid component comprising a monomer of an acrylic ester and (b) a powdered component comprising, based on the weight of the powdered component, (i) from 0 to about 20 percent of a methyl methacrylate homopolymer, (ii) from about 30 to about 60 percent of a methyl methacrylatestyrene copolymer, and (iii) from about 30 to about 60 percent of a methyl methacrylate-butyl methacrylate copolymer. Opacifying agents can be incorporated in the powdered component.

The existing bone cement compositions are usually hand mixed at the time of surgery, resulting in materials with a maximum tensile strength of approximately 30 MPa and a maximum tensile deformation of approximately 0.015 strain. With the introduction of new methods of mixing the cement, such as vacuum mixing and centrifugation, improvements in the tensile strength of the bone cement have been reported. While useful for their intended purpose, it would also be highly desirable to have a bone cement composition exhibiting higher maximum tensile deformation, that is, the ability to sustain higher strains without failure.

Since the terpolymer according to the present invention allows the optimum amount of the desired chemical groups in a single polymer chain, it presents a more specific way of varying the mechanical properties of the bone cement.

SUMMARY OF THE INVENTION

In accordance with the present invention, there is disclosed a bone cement composition comprising:
(a) a liquid component comprising a monomer of an acrylic ester, and
(b) a powdered component comprising a terpolymer of methyl methacrylate, butyl methacrylate, and styrene.

Additional agents such as free radical stabilizers, for example, hydroquinone, and polymerization accelerators, such as, for example, N,N-dimethyl paratoluidine, may also be incorporated in component (a).

In a preferred embodiment, the bone cement composition comprises, based on the weight of the powdered component, a terpolymer of 55 to 89.5% methyl methacrylate, 10 to 40% butyl methacrylate, and 0.5 to 5.0% styrene.

Opacifying agents can also be incorporated in the powdered component.

In a further embodiment, the present invention is directed to a powdered component useful as a precursor for a bone cement composition comprising a terpolymer of methyl methacrylate, butyl methacrylate, and styrene.

The present invention is also directed to a process for the production of a bone cement composition comprising combining:
(a) a liquid component comprising a monomer of an acrylic ester with (b) a powdered component comprising a terpolymer of methyl methacrylate, butyl methacrylate, and styrene.

In another embodiment, the present invention is directed to a process for the production of a powdered component useful as a precursor for a bone cement composition comprising a terpolymer of methyl methacrylate, butyl methacrylate, and styrene.

BRIEF DESCRIPTION OF THE DRAWING

The FIGURE shows a stress-strain curve of a bone cement made from a terpolymer of the present invention.

DETAILED DESCRIPTION OF THE INVENTION

Component (a) of the bone cement composition of the present invention comprises a liquid monomer of an acrylic ester. By the term "acrylic ester", it is meant the acrylates, preferably having a $C_1$–$C_4$ alkyl group in the ester moiety. One especially preferred acrylic ester is methacrylate with an especially preferred liquid monomer being methyl methacrylate. This liquid monomer is represented by the formula:

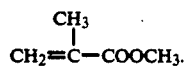

In addition, the liquid monomer may contain a polymerization accelerator such as N,N-dimethyl paratoluidine. Additionally, the liquid monomer may also contain a free radical stabilizer such as hydroquinone. The hydroquinone functions to prevent premature polymerization which may occur under conditions such as heat, light or chemical reagents.

The powdered component of the bone cement composition is a terpolymer of methyl methacrylate, butyl methacrylate, and styrene and preferably has an average molecular weight of from about 500,000 to about 1,500,000. The preferred ranges, based on the weight of the powdered component, are 55 to 89.5% methyl methacrylate, 10–40% butyl methacrylate and 0.5 to 5% styrene. The particle size distribution in the styrene, methyl methacrylate, butyl methacrylate terpolymer can range from about 50 to about 500 microns preferably with 50% of the particles being between 100 and 200 microns.

A methyl methacrylate, butyl methacrylate, styrene terpolymer is a polymer that has within a single polymeric chain a random sequence of the following chemical groups:

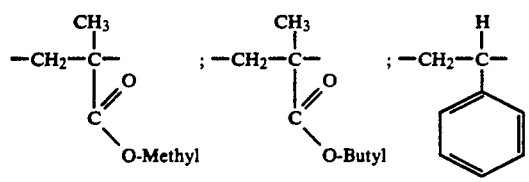

The proportion of each chemical group within the polymer chain is determined by the initial amount of reacting monomers.

The powdered component may also contain an opacifying agent. The opacifying agent may be selected from any of those known for this purpose. Representative examples include barium sulphate, zinc oxide and zirconium oxide. Preferably, the opacifying agent will be added at a concentration of from about 5 to about 10 percent by weight of the powdered component.

Additional agents, such as colorants, extra catalysts, antibiotics, etc., may also be added to the powdered component.

Liquid component (a) and powdered component (b) are combined under sterile conditions to yield the bone cement composition. Preferred methods of sterilization include irradiation, especially for the powdered component, and bacteriological filtration for the liquid monomer.

Although the present invention has been described in relation to the combination of liquid component (a) and powdered component (b) to form a bone cement composition, it will be apparent to those skilled in the art that powdered component (b) comprising a terpolymer of methyl methacrylate, butyl methacrylate, and styrene per se also forms a part of the present invention. The present invention is also directed to a process for the production of the bone cement composition of the present invention. The bone cement composition is formed by combining (a) the liquid component previously described with (b) the powdered component previously described. The order of addition of each component to form the bone cement composition is not critical, although it is usually preferred to add the liquid component to the powdered component. In addition, the present invention also embraces a process for the production of a powdered component useful as a precursor for a bone cement composition. Having described the invention in general terms, reference is now made to specific examples thereof. It is to be understood that these examples are not meant to limit the present invention, the scope of which is determined by the appended claims.

EXAMPLE

Bone cement compositions were prepared by combining the two components as follows:

(A) 20 ml of methyl methacrylate; and
(B) 40 grams of a terpolymer of methyl methacrylate, butyl methacrylate, and styrene.

Component B was prepared in 3 different molecular weights (Mw), labeled: Formulations (1), (2) and (3) (Mw: 1,337,000; Mw: 845,900; and Mw: 611,000 respectively).

The suspension polymerization process for forming the terpolymer beads of formulation (1) was as follows:

1) A 5% polyvinyl alcohol solution was made by dispersing 15 grams of polyvinyl alcohol (Air Products Airvol 523) in 285 grams of deionized cold water. The solution was heated to 80.C and allowed to cool to room temperature(22 C).

2) Then 300 grams of the solution was added to a 5 liter flask containing 2700 grams deionized water and equipped with a stirrer, condenser, and argon sparge. The flask was placed in a water bath and sparged with stirring for 1 hour.

3) Separately, a monomer mix was prepared as follows: 924 grams of methyl methacrylate (Rohm and Haas 10 PPM MEHQ) was mixed with 240 grams of butyl methacrylate (Rohm & Haas 10ppm MEHQ) and 36 grams of styrene (Eastman Kodak 10–15ppm tBC). 14.4 grams of benzoyl peroxide (Aldrich Chemical) was then added and the mixture was shaken until all components dissolved.

4) The stirrer speed was adjusted to between 150-200 rpm. The monomer mix above was then added to the flask in a thin stream.

5) The mixture was reacted at 55° C. for 18 hours. It was then cooled by pouring it into 5 volumes of room temperature water and allowed to settle for 1 hour.

6) The supernatant milky liquid containing very small particles of the terpolymer was decanted. 5 volumes of fresh water was then added. This step was then repeated until the supernatant was clear.

7) The terpolymer was filtered on a glass frit, washed with several volumes of water, and then air dried to remove the bulk of the water in a circulating air oven.

8) The terpolymer was then dried in a vacuum oven for 24 hours at 50° C.

9) The terpolymer was then sieved through a 1 mm screen to remove any coagulum and fused particles.

A terpolymer of, by weight, 77% methyl methacrylate, 20% butyl methacrylate and 3% styrene, and having a molecular weight of 1,337,000 was produced. Following the procedure outlined above, formulations 2 and 3 were prepared, but with the following amount of reactants:

Formulation 2

1500 g H₂O
150 g 5% Polyvinylalcohol
385 g Methyl Methacrylate
100 g Butyl Methacrylate
15 g Styrene
5 g Benzoyl Peroxide This formulation resulted in a terpolymer with a molecular weight of 845,900.

Formulation 3

3000 g H₂O
120 g 5% Polyvinylalcohol
770 g Methyl Methacrylate
200 g Butyl Methacrylate
30 g Styrene
12 g Benzoyl Peroxide This formulation resulted in a terpolymer with a molecular weight of 611,000.

All monomers used in step 3 are low inhibitor grade and can be used as received as long as care is taken to sparge the solution thoroughly with Argon. An industrial grade Argon is sufficient unless the Oxygen content exceeds 5ppm. Nitrogen would work as well.

The ultimate particle size may be somewhat dependent on stirring, but as is apparent to one skilled in the art, the particle size can be largely controlled by the polyvinyl alcohol concentration. Molecular weight can be controlled by adjusting the bath temperature and benzoyl peroxide concentration. Molecular weight varies inversely with temperature so that a higher molecular weight results from a lowered temperature.

Component B was sterilized by gamma irradiation prior to mixing. After mixing component A and formulations 1, 2 and 3 of component B, the compositions were allowed to set and were then tested against control Simplex ® P for their resistance to stress and strain.

Description of Tensile Test

The axial tensile properties of these materials are determined according to ASTM-D-638-72 (Standard Method of Test for Tensile Properties of Plastics).

Specimen Preparations

The powdered and liquid components were hand mixed for approximately 2 minutes in the barrel of an Exeter ® cement gun. The cement was extruded into aluminum molds where it is allowed to set.

The resulting specimens were standard type IV flat tensile bars.

The tensile bars were aged for seven days in saline solution at 37° C.

Testing

Testing was carried out at room temperature in an Instron 1122 testing unit with a cross head speed of 5mm per minute.

Deformation was determined with a 10% maximum elongation extensometer. Strain was calculated from the elongation at failure.

Stress was calculated from the load at failure.

Modulus was calculated from the initial slope of the load versus deformation curve.

The test results are shown in Table I and FIG. I.

TABLE I

| Formulation[1] | ASTM-D-638-72 | | | | | |
|---|---|---|---|---|---|---|
| | Stress | Δ%* | Strain | Δ%* | Modulus | Δ%* |
| Simplex ® P | 28.3 MPa | | 0.0140 | | 2,450 MPa | |
| Component B: | | | | | | |
| Formulation 1 | 30.7 MPa | +8 | 0.0200 | +43 | 2,030 MPa | −17 |
| Formulation 2 | 23.5 MPa | −17 | 0.0150 | +7 | 1,870 MPa | −24 |
| Formulation 3 | 18.6 MPa | −34 | 0.0170 | +21 | 1,560 MPa | −36 |

[1]A formulation consists of 20 ml of liquid methyl methacrylate monomer (component A) and 40 g of powder (component B).
*are percentage differences from control.

While the percentages by weight of the powdered terpolymer tested were 77% methyl methacrylate, 20% butyl methacrylate and 3% styrene, any terpolymer comprising, by weight of the powdered component, of between 55 to 89.5% methyl methacrylate, 10 to 40% butyl methacrylate and 0.5 to 5% styrene, is also suitable.

The figure displays a plot of stress vs. strain of Simplex ® P vs. the bone cement of Table I made with the powdered component (B) utilizing the terpolymer of formulation 1.

While several examples of the present invention have been described, it is obvious that many changes and modifications may be made thereunto, without departing from the spirit and scope of the invention.

I claim:

1. A bone cement composition comprising:
   (a) a liquid component comprising a monomer of an acrylic ester, and
   (b) a powdered component comprising a terpolymer of methyl methacrylate, butyl methacrylate, and styrene wherein the powdered component comprises, based on the weight of the powdered component, 55 to 89.5% methyl methacrylate, 10 to 40% butyl methacrylate, and 0.5 to 5% styrene.

2. The composition of claim 1 further comprising a free radical stabilizer and a polymerization accelerator incorporated in component (a).

3. The composition of claim 2 wherein said free radical stabilizer is hydroquinone and said polymerization accelerator N-dimethyl paratoluidine.

4. The composition of claim 1 further comprising an opacifying agent in the powdered component.

5. The composition of claim 1 wherein the particle size distribution in the methyl methacrylate, butyl methacrylate and styrene terpolymer ranges between 50 to 500 microns.

6. The composition of claim 5 wherein at least 50% of the particles range between about 100 and 200 microns.

7. The composition of claim 5 wherein the powdered component comprises, based on the weight of the powdered component, 77% methyl methacrylate, 20% butyl methacrylate and 3% styrene and has a molecular weight greater than 1,000,000.

8. A process for the production of a bone cement composition comprising combining:
   (a) a liquid component comprising a monomer of an acrylic ester, and
   (b) a powdered component comprising a terpolymer of methyl methacrylate, butyl methacrylate, and styrene wherein the powdered component comprises, based on the weight of the powdered component, 55 to 89% methyl methacrylate, 10 to 40% butyl methacrylate, and 0.5 to 5% styrene.

* * * * *